United States Patent [19]

Kiener et al.

[11] Patent Number: 5,306,630

[45] Date of Patent: Apr. 26, 1994

[54] MICROBIOLOGICAL PROCESS FOR HYDROXYLATION OF NITROGEN-HETEROCYCLIC-CARBOXYLIC ACIDS

[75] Inventors: Andreas Kiener, Visp; Andreas Tschech, Aarau; Andreas Tinschert, Brig; Klaus Heinzmann, Visperterminen, all of Switzerland

[73] Assignee: Lonza Ltd., Gampel-Valais, Switzerland

[21] Appl. No.: 24,768

[22] Filed: Mar. 2, 1993

[30] Foreign Application Priority Data

Mar. 4, 1992 [CH] Switzerland ............................ 672/92

[51] Int. Cl.$^5$ .................... C12P 17/12; C12P 7/42; C12N 1/12; C12N 1/20
[52] U.S. Cl. ...................... 435/122; 435/117; 435/121; 435/128; 435/146; 435/136; 435/252.1; 435/822
[58] Field of Search ...................... 435/122, 146, 252.1

[56] References Cited

U.S. PATENT DOCUMENTS

| | | | |
|---|---|---|---|
| 4,081,451 | 3/1978 | Mayer | 260/295.5 |
| 4,738,924 | 4/1988 | Kulk et al. | 435/122 |
| 5,082,777 | 1/1992 | Lehky et al. | 435/122 |
| 5,151,351 | 9/1992 | Hooks et al. | 435/122 |
| 5,217,884 | 6/1993 | Zimmermann et al. | 435/122 |
| 5,229,278 | 7/1993 | Kiener et al. | 435/122 |
| 5,236,832 | 8/1993 | Kiener | 435/122 |
| 5,238,829 | 8/1993 | Kiener | 435/122 |
| 5,238,830 | 8/1993 | Kiener et al. | 435/122 |
| 5,242,816 | 9/1993 | Kiener | 435/122 |

FOREIGN PATENT DOCUMENTS

| | | | |
|---|---|---|---|
| 2060534 | 8/1992 | Canada | 435/122 |
| 0498316A2 | 8/1992 | European Pat. Off. | 435/122 |
| 0519512 | 12/1992 | European Pat. Off. | 435/122 |
| 4-304893 | 10/1992 | Japan | 435/122 |
| 4-304894 | 10/1992 | Japan | 435/122 |

OTHER PUBLICATIONS

Dubok (1991) J. Heterocyclic Chem, 28, 1131–1137.
Gage et al. (1982) J. Heterocyclic Chem, 19, 401–406.
Weiner et al. (1972) J. Pharmacol Exp Ther, 180, 411–434.
Chemical Abstracts, 94:15515m, (1981).

Primary Examiner—David M. Naff
Assistant Examiner—Jeffrey J. Sevigny
Attorney, Agent, or Firm—Fisher, Christen & Sabol

[57] ABSTRACT

A new microbiological process for the production of hydroxy-nitrogen-heterocyclic-carboxylic acids or their soluble salts of the general formula:

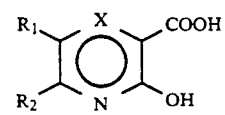

wherein $R_1$ and $R_2$ are the same or different and each is a hydrogen atom, a halogen atom or a $C_1$–$C_4$ alkyl group and X is a nitrogen atom or a $CR_3$ function, wherein $R_3$ is a hydrogen atom or a halogen atom, starting from the corresponding nitrogen-heterocyclic-carboxylic acids, as well as new microorganisms suitable for use in the process.

7 Claims, No Drawings

MICROBIOLOGICAL PROCESS FOR HYDROXYLATION OF NITROGEN-HETEROCYCLIC-CARBOXYLIC ACIDS

BACKGROUND OF THE INVENTION

1. Field Of The Invention

The invention relates to a new microbiological process for the production of hydroxy-nitrogen-heterocyclic-carboxylic acids or their soluble salts of the general formula:

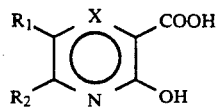

wherein $R_1$ and $R_2$ are the same or different and each is a hydrogen atom, a halogen atom or a $C_1$-$C_4$ alkyl group and X is a nitrogen atom or a $CR_3$ function, wherein $R_3$ is a hydrogen atom or a halogen atom, starting from the corresponding nitrogen heterocyclic-carboxylic acids, as well as new microorganisms suitable for use in the process.

In the following material, it is to be understood that the category of nitrogen-heterocyclic-carboxylic acids, hydroxylated or not hydroxylated, also includes the soluble salts thereof, such as, their alkali or ammonium salts.

2. Background Art

2-Hydroxy-nitrogen-heterocyclic-carboxylic acids are important intermediate products in active ingredient syntheses. For example, 2-hydroxynicotinic acid can be used as the initial material for the production of 2-chloronicotinic acid (U.S. Pat. No. 4,081,451) which, for example, represents an important intermediate product for the production of pharmaceutical agents Chemical Abstracts, 94:155515m(1981) which abstracts [Ann. Pharm. Fr., 38(3), (1980), pp. 243 to 252].

Until now no microbiological processes for the production of hydroxy-nitrogen-heterocyclic-carboxylic acids were known.

BROAD DESCRIPTION OF THE INVENTION

The object of the invention was to provide a simple, ecological microbiological process for the production of 2-hydroxy-nitrogen-heterocyclic-carboxylic acids, which is chemically difficult to achieve. Other objects and advantages of the invention are set out herein or are obvious herefrom to one skilled in the art.

The objects and advantages of the invention are achieved by the process, microorganisms and compounds of the invention.

The invention includes a microbiological process for the production of hydroxy-nitrogen-heterocyclic-carboxylic acids or their soluble salts of the general formula:

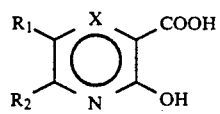

wherein $R_1$ and $R_2$ are the same or different and each is a hydrogen atom, a halogen atom or a $C_1$-$C_4$ alkyl group and X is a nitrogen atom or a $CR_3$ function, wherein $R_3$ is a hydrogen atom or a halogen atom. A nitrogen-heterocyclic-carboxylic acid or its soluble salts of the general formula:

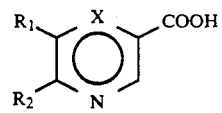

where $R_1$, $R_2$ and X have the above-stated meanings, as the substrate, is/are converted by microorganisms utilizing 6-methylnicotinic acid, containing a specific hydroxylase, into the product according to formula I.

Preferably the nitrogen-heterocyclic-carboxylic acids of the general formula:

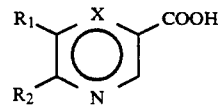

wherein $R_1$ and $R_2$ are the same or different and each is a hydrogen atom, a chlorine atom or a methyl group and X is a nitrogen atom or a CH function, are used as the substrate. Preferably the reaction is performed with microorganisms of the designation Ki101 (DSM 6920) or their descendants or their mutants. Preferably the reaction takes place by a one-time or continuous substrate addition so that the substrate concentration in the culture medium does not exceed 10 percent by weight. Preferably the reaction is performed at a temperature of 15° to 50° C. and at a pH of 5 to 9.

The invention also involves microorganisms that are selected so that they utilize 6-methylnicotinic acid as the sole carbon, nitrogen and energy source over 2-hydroxy-6-methylnicotinic acid. Biologically-pure cultures of such microorganisms are included. Preferably the microorganisms are the microorganisms with the designation Ki101 (DSM 6920) as well as their descendants or their mutants, including biologically-pure cultures of such microorganisms.

The invention further involves hydroxy-nitrogen-heterocyclic-carboxylic acids of the general formula:

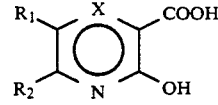

wherein, if X is a nitrogen atom, $R_1$ and $R_2$ are the same or different and each is a hydrogen atom, a halogen atom or a $C_1$-$C_4$ alkyl group, with the exception that $R_1$ and $R_2$ both are not hydrogen at the same time, and, if X is a CH function, $R_1$ and $R_2$ both are a chlorine atom. Preferably such hydroxy-nitrogen-heterocyclic-carboxylic acids are 5,6-dichloro-2-hydroxynicotinic acid, 3-hydroxy-5-methylpyrazine carboxylic acid or 3-hydroxy-5-chloropyrazine carboxylic acid.

DETAILED DESCRIPTION OF THE INVENTION

According to the invention the process is carried out so that a nitrogen-heterocyclic-carboxylic acid of the general formula:

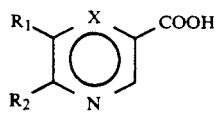

wherein $R_1$ and $R_2$ are the same or different and each is a hydrogen atom, a halogen atom or a $C_1$-$C_4$ alkyl group and X is a nitrogen atom or a $CR_3$ function, wherein $R_3$ is a hydrogen atom or a halogen atom, as the substrate, is converted by microorganisms utilizing 6-methylnicotinic acid, containing a specific hydroxylase, into the hydroxy-nitrogen-heterocyclic-carboxylic acid of general formula:

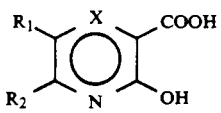

wherein $R_1$, $R_2$ and X have the above-stated meaninqs.

The following is a description of what is meant by the term "microorganisms utilizing 6-methylnicotinic acid, containing a specific hydroxylase":

If a biomass is cultivated, for example, from sewage sludge as an inoculum with 6-methylnicotinic acid, microorganisms utilizing 6-methylnicotinic acid, i.e., microorganisms that grow with 6-methylnicotinic acid as the sole carbon, nitrogen and energy source, are obtained. If the microorganisms are now selected according to methods usual to one skilled in the art, which completely catabolize 6-methylnicotinic acid by 2-hydroxy-6-methylnicotinic acid as the intermediate product, microorganisms are obtained that contain a specific hydroxylase, i.e., microorganisms that specifically hydroxylate the sole carbon atom present between the acid function and the nitrogen atom.

In principle, all microorganisms are suitable for the invention process that are selected according to this principle, for example, from sewage sludge or soil samples. These microorganisms are not described in the literature and are a component of the invention.

Suitably the microorganisms with the designation Ki101 (DSM 6920) as well as their descendants and mutants are used for the process. These microorganisms were deposited on Feb. 10, 1992 with the Deutsche Sammlung für Mikroorganismen und Zellkulturen GmbH (German Collection for Microorganisms and Cell Cultures, Limited Liability Company), Mascheroderweg 1b, D-3300 Brunswick, Germany.

A scientific (taxonomic) description of Ki101 (DSM 6920) is:

| cell shape | tiny rods |
|---|---|
| width, micron | 0.4–0.5 |
| length, micron | 1.0–1.5 |
| mobility | − |
| flagella | − |
| gram reaction | − |
| lysis by 3% KOH | + |
| aminopeptidase (Cerny) | + |
| spores | − |
| oxidase | + |
| catalase | + |

A genus could not be determined by 16S rRNA-sequence analysis.

The selection and cultivation of these microorganisms, with 6-methylnicotinic acid, takes place according to methods usual to one skilled in the art. Suitably the "screening" for the microorganisms takes place under aerobic conditions during the selection. Preferably the microorganisms are cultivated dormant (not with shaking) during the "screening."

The amount of 6-methylnicotinic acid used during the selection and the cultivation suitably is up to 1 percent by weight, preferably up to 0.5 percent by weight. The selection and cultivation are suitably performed at a pH of 5 to 9, preferably of 6 to 8. The temperature during the selection and the cultivation suitably is between 15° and 50° C., preferably between 25° and 40° C.

Usually the selection and cultivation take place in a mineral salt medium, preferably in the mineral salt medium whose composition is described in Table 1 below.

If a suitable optical density at 650 nm ($OD_{650}$) of 0.5 to 100 is reached, the microorganisms either can be harvested according to methods usual to one skilled in the art or the substrate, the nitrogen-heterocyclic-carboxylic acid, can be directly added to the microorganisms for the actual reaction (biotransformation).

The actual biotransformation then takes place in a way usual to one skilled in the art with nongrowing cells.

As the substrate of general formula II, for example, nicotinic acid, pyrazine carboxylic acid or their halogenated or $C_1$-$C_4$ alkylated derivatives can be used. As the halogenated nicotinic acid or pyrazine carboxylic acid derivatives, preferably 6-chloronicotinic acid, 5,6-dichloronicotinic acid and 5-chloropyrazine carboxylic acid are hydroxylated. As the $C_1$-$C_4$ pyrazine carboxylic acid derivatives, preferably 5-methylpyrazine-carboxylic acid is hydroxylated.

The substrate for the biotransformation can be added continuously or all at once. Suitably the substrate addition takes place so that the substrate concentration in the culture medium does not exceed 10 percent by weight, preferably 7 percent by weight.

As the medium for the biotransformation, those usual to one skilled in the art can be used. Preferably the biotransformation is performed in a low-molar phosphate buffer. Usually the biotransformation is performed with a microorganism-suspension that has an optical density at 650 nm ($OD_{650}$) of 0.5 to 100, preferably of 5 to 50. Suitably the biotransformation is performed at a temperature of 15° to 50° C., preferably of 25° to 35° C., and a pH of 5 to 9, preferably 6.5 to 7.5.

After a usual reaction time of 5 hours up to 3 days, the hydroxylated product according to formula 1 can then be isolated according to methods usual to one skilled in the art, for example, by acidification of the cell-free supernatant.

The hydroxy-nitrogen-heterocyclic-carboxylic acids—(produced according to the invention process) of general formula:

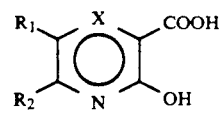

wherein, if X is a nitrogen atom, $R_1$ and $R_2$ are the same or different and each is a hydrogen atom, a halogen atom or a $C_1$-$C_4$ alkyl group, with the exception that $R_1$ and $R_2$ together do not mean hydrogen, as well as if X is a CH function, $R_1$ and $R_2$ are each a halogen atom, are not described in the literature. The preferred representatives of these new compounds are 5,6-dichloro-2-hydroxynicotinic acid, 3-hydroxy-5-methylpyrazine-carboxylic acid and 3-hydroxy-5-chloropyrazine carboxylic acid.

EXAMPLE 1

Isolation of microorganisms using 6-methyl-nicotinic acid

A 300 ml Erlenmeyer flask was filled with 100 ml of mineral salt medium containing 1 mmol of 6-methyl-nicotinic acid (Table 1 below) and mixed with 10 ml of sewage sludge from the LONZA AG sewage treatment plant in Visp, Switzerland or with soil samples from the LONZA-Werk, Visp and incubated dormant at 30° C. The catabolism of 6-methylnicotinic acid was observed with UV-spectrum at 200 to 400 mm. After 10 days 2-hydroxy-6-methylnicotinic acid was spectrophotometrically detectable in some batches. These cultures were then inoculated several times in fresh mineral salt medium. Then the cell suspensions forming 2-hydroxy-6-methylnicotinic acid were plated out on the same medium, containing 1.6 percent (w/v) of agar. The agar plates were then incubated at 30° C. in an atmosphere containing 4 percent of $O_2$ and 96 percent of $N_2$. Individual colonies were then transferred in liquid medium and incubated dormant. The bacteria strain with the designation Ki101 (DSM 6920) during the growth on 6-methyl-nicotinic acid formed 2-hydroxy-6-methyl-nicotinic acid.

EXAMPLE 2

Microbial oxidation of nicotinic acid to 2-hydroxynicotinic acid

The microorganisms with the designation Ki101 (DSM 6920) were incubated in 800 ml of mineral salt medium (Table 1 below) with addition of 8 mmol of 6-methylnicotinic acid in a 1 l Fernbach flask at 30° C. on a shaker at 100 rpm. The inoculum was 5 percent (v/v). After 5 days, the $OD_{650}$ was about 0.5. Then the cells were harvested and washed once with 50 m molar phosphate buffer, pH 7.0. Then the cells were resuspended in 20 ml of 50 mM of phosphate buffer, pH 7.0 containing 200 mg (1.38 mmol) of nicotinic acid-sodium salt. The $OD_{650}$ was 20. After 6 hours incubation on a shaker at 30° C., no more nicotinic acid could be detected by thin-layer chromatography. Then the biomass was centrifuged off and the supernatant acidified to pH 2.5 to precipitate the 2-hydroxynicotinic acid. No contamination in the isolated product could be detected by $^1$H-NMR (DMSO) analysis. Altogether 140 mg (1 mmol) of 2-hydroxynicotinic acid corresponding to a yield of 72 percent relative to nicotinic acid could be isolated.

TABLE 1

| Mineral salt medium stock solutions | |
|---|---|
| Stock solution 1: | |
| $NaH_2PO_4.2H_2O$ | 156.0 g |
| $NH_4Cl$ | 10.0 g |
| $K_2SO_4$ | 1.2 g |
| pH to be adjusted with KOH to | 7.0 |
| distilled water 500.0 ml | |
| Stock solution 2: | |
| p-aminobenzoic acid | 8.0 mg |
| D-biotin | 2.0 mg |

TABLE 1-continued

| Mineral salt medium stock solutions | |
|---|---|
| nicotinic acid | 20.0 mg |
| Ca-D-pantothenate | 10.0 mg |
| pyridoxalhydrochloride | 30.0 mg |
| thiamindichloride | 20.0 mg |
| cyanocobalamin | 10.0 mg |
| distilled water 100.0 ml, to be sterilized by filtration | |
| Stock solution 3: | |
| HCl (37%) | 7.0 ml |
| $FeCl_2.4H_2O$ | 1.5 g |
| $ZnCl_2$ | 0.07 g |
| $MnCl_2.4H_2O$ | 0.1 g |
| $H_3BO_3$ | 0.006 g |
| $CoCl_2.6H_2O$ | 0.19 g |
| $CuCl_2.7H_2O$ | 0.002 g |
| $NiCl_2.6H_2O$ | 0.024 g |
| $Na_2MoO_4.2H_2O$ | 0.036 g |
| distilled water 1000.0 ml, to be autoclaved, 121°, 20 min. | |
| Stock solution 4: | |
| NaOH | 0.5 g |
| $Na_2SeO_3.5H_2O$ | 0.003 g |
| $Na_2WO_4.2H_2O$ | 0.004 g |
| distilled water 1000.0 ml, to be autoclaved, 121°, 20 min. | |
| Stock solution 5: | |
| $MgCl_2.6H_2O$ | 40.0 g |
| $CaCl_2.2H_2O$ | 5.0 g |
| distilled water 200.0 ml, to be autoclaved, 121°, 20 min. | |
| 6-methylnicotinic acid (500 mM) | |
| 6-methylnicotinic acid-sodium salt | 80.0 g |
| distilled water 1000.0 ml, to be autoclaved, 121°, 20 min. | |
| Growth medium 10 mM of 6-methylnicotinic acid | |
| solution 1 | 25.0 ml |
| 6-methylnicotinic acid | 20.0 ml |
| distilled water 1000.0 ml, to be autoclaved, 121°, 20 min. | |
| After the sterilization | |
| solution 2 | 0.5 ml |
| solution 3 | 1.0 ml |
| solution 4 | 1.0 ml |
| solution 5 | 0.5 ml were added. |

EXAMPLES 3 TO 7

Examples 3 to 7 were performed corresponding to Example 2. The results are compiled in Table 2.

TABLE 2

| Example | Initial Material | Conc. | $OD_{650}$ nm | Time [h] |
|---|---|---|---|---|
| 3 | 6-chloronicotinic-acid-sodium salt | 1% (w/v) | 20 | 16 |
| 4 | 5,6-dichloronicotinic-acid-sodium salt | 1% (w/v) | 20 | 16 |
| 5 | pyrazine-carboxylic acid-sodium salt | 0.3% (w/v) | 5 | 24 |
| 6 | 5-methyl-pyrazine-carboxylic acid-sodium salt | 0.3% (w/v) | 5 | 24 |
| 7 | 5-chloro-pyrazine-carboxylic acid-sodium salt | 0.3% (w/v) | 5 | 24 |

| Example | Product | Yield | |
|---|---|---|---|
| 3 | 6-chloro-2-hydroxynicotinic acid | 70% | (isolated) |
| 4 | 5,6-dichloro-2-hydroxynicotinic acid | 20% | (analytic) |
| 5 | 3-hydroxypyrazine carboxylic acid | 70% | (analytic) |
| 6 | 3-hydroxy-5-methyl-pyrazine-carboxylic acid | 80% | (analytic) |
| 7 | 3-hydroxy-5-chloro-pyrazine-carboxylic acid | 50% | (analytic) |

Analytical data for Example 6

3-Hydroxy-5-methyl-pyrazine carboxylic acid $^1$H-NMR (DMSO, 400 MHz) δ in ppm 2.4, s; 2.6, s; 3.8, s; 7.8, s.

$^{13}$C-NMR (DMSO, 100.5 MHz) δ in ppm 20, t; 40, m; 130, s; 134, s; 155, s; 164, s; 170, s.

Analytical data for Example 7

3-Hydroxy-5-chloro-pyrazine carboxylic acid $^1$H-NMR: (D$_2$O and dioxane, 400 MHz) δ in ppm 3.8, s; 4.7, s; 8.0, s.

$^{13}$C-NMR (D$_2$O and dioxane, 100.5 MHz) δ in ppm 132, s; 133, s; 145, s; 149, s; 164, s; 172, s.

What is claimed is:

1. A microbiological process for the production of a hydroxy-nitrogen-heterocyclic-carboxylic acid or a soluble salt thereof of the formula:

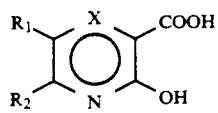

wherein R$_1$ and R$_2$ are the same or different and each is a hydrogen atom, a halogen atom or a C$_1$-C$_4$ alkyl group and X is a nitrogen atom or a CR$_3$ group, wherein R$_3$ is a hydrogen atom or a halogen atom, comprising converting a nitrogen-heterocyclic-carboxylic acid or a soluble salt thereof of the formula:

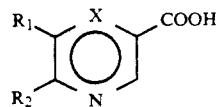

wherein R$_1$, R$_2$ and X have the above-stated meanings, into the product according to formula I by microorganism DSM 6920 or a mutant thereof which is capable of effecting said conversion, said microorganisms DSM 6920 or said mutant thereof being capable of utilizing 6-methylnicotinic acid and containing a hydroxylase which specifically hydroxylates the sole carbon atom between the acid function and the nitrogen atom of the compound according to formula II.

2. The process according to claim 1, wherein a nitrogen-heterocyclic-carboxylic acids of the formula:

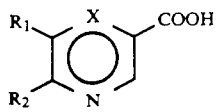

wherein R$_1$ and R$_2$ are the same or different and each is a hydrogen atom, a chlorine atom, or a methyl group and X is a nitrogen atom or a CH function, is used as the substrate.

3. The process according to claim 2 wherein the reaction takes place by a one-time or continuous substrate addition so that the substrate concentration in the culture medium does not exceed 10 percent by weight.

4. The process according to claim 3 wherein the reaction is performed at a temperature of 15° to 50° C. and at a pH of 5 to 9.

5. The process according to claim 1 wherein the reaction takes place by a one-time or continuous substrate addition so that the substrate concentration in the culture medium does not exceed 10 percent by weight.

6. The process according to claim 1 wherein the reaction is performed at a temperature of 15° to 50° C. and at a pH of 5 to 9.

7. A biologically pure culture of microrganisms DSM 6920 or mutant thereof, which utilizes 6-methylnicotinic acid as the sole carbon, nitrogen and energy source and is capable of converting a nitrogen-heterocyclic-carboxylic acid or a soluble salt thereof of the formula:

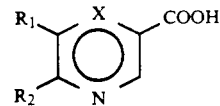

wherein R$_1$ and R$_2$ are the same or different and each is a hydrogen atom, a halogen atom or a C$_1$-C$_4$ alkyl group, and X is a nitrogen atom or a CR$_3$ group, wherein R$_3$ is a hydrogen atom or a halogen atom, into a hydroxy-nitrogen-heterocyclic-carboxylic acid or a soluble salt thereof of the formula:

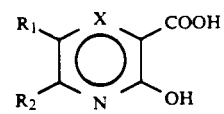

wherein R$_1$, R$_2$ and X have the above-stated meanings.

* * * * *